United States Patent [19]

Lesher et al.

[11] Patent Number: 4,532,247

[45] Date of Patent: Jul. 30, 1985

[54] 5-(HYDROXYALKYL OR ALKANOYLOXYMETHYL)-1,6-NAPHTHYRIDIN-2(1H)-ONE AND CARDIOTONIC USE THEREOF

[75] Inventors: George Y. Lesher, Schodack; Baldev Singh, East Greenbush, both of N.Y.

[73] Assignee: Sterling Drug Inc., New York, N.Y.

[21] Appl. No.: 521,293

[22] Filed: Aug. 8, 1983

[51] Int. Cl.$^3$ .................... A61K 31/44; C07D 471/04
[52] U.S. Cl. .................................. 514/299; 546/122
[58] Field of Search ........................ 546/122; 424/256

[56] References Cited

PUBLICATIONS

Traynelis et al., Chem. Abst., vol. 54, 3410a, (1960).
Chemical Abstracts 72, 12,615d, (1970).
Ogata et al., [Chem. Pharm. Bull. 20, 2264, (1972)].

*Primary Examiner*—Henry R. Jiles
*Assistant Examiner*—Bernard L. Dentz
*Attorney, Agent, or Firm*—Robert K. Bair; B. Woodrow Wyatt; Paul E. Dupont

[57] ABSTRACT

4-R'-5-Q-1,6-naphthyridin-2(1H)-ones (I), where R' is hydrogen or methyl and Q is hydroxymethyl, 1-hydroxyethyl alkanoyloxymethyl or 1-alkanoyloxyethyl, are produced by first reacting 4-R'-5-acetyl(or n-propanoyl)-6-[2-(di-lower-alkylamino]-2(1H)-pyridinone [III] with hydroxylamine or salt thereof to produce 4-R'-5-Q'-1,6-naphthyridin-2(1H)-one-6-oxide (II), where R' is defined as above and Q' is methyl or ethyl; next reacting II with an alkanoic anhydride to produce I where Q is alkanoyloxymethyl or 1-alkanoyloxyethyl; and, then hydrolyzing said alkanoyloxymethyl or -ethyl compound to produce I where Q is hydroxymethyl or 1-hydroxyethyl. Also shown is the cardiotonic use of II and I where Q is hydroxymethyl, 1-hydroxyethyl or alkanoyloxymethyl.

7 Claims, No Drawings

5-(HYDROXYALKYL OR ALKANOYLOXYMETHYL)-1,6-NAPHTHYRIDIN-2(1H)-ONE AND CARDIOTONIC USE THEREOF

CROSS-REFERENCE TO RELATED APPLICATIONS

Copending application Ser. No. 404,454, filed Aug. 2, 1982 and now U.S. Pat. No. 4,415,580, issued Nov. 15, 1983, discloses and claims 4-R'-5-Acetyl-6-[2-($R_1R_2$N)-ethenyl]-2(1H)-pyridinones and the corresponding 5-n-propanoyl homologs, where R' is hydrogen or methyl and $R_1$ and $R_2$ are each lower-alkyl, as well as their cardiotonic use.

Copending application Ser. No. 502,858, filed June 9, 1983 as a continuation-in-part of said application Ser. No. 404,454 discloses and claims 4-R'-5-(lower-alkyl)-1,6-naphthyridin-2(1H)-ones, their preparation and cardiotonic use, where R' is hydrogen or methyl.

BACKGROUND OF THE INVENTION

1. Field of the Invention

This invention relates to 5-hydroxymethyl-1,6-naphthyridin-2(1H)-ones, alkanoate esters thereof, 5-methyl(or ethyl)-1,6-naphthyridin-2(1H)-one 6-oxides, and the cardiotonic use thereof.

2. Information Disclosure Statement

Chemical Abstracts 72, 12,615d (1970) is reproduced as follows: "Chemotherapeutics. IV. 1,6-Naphthyridine N-oxides. Takahashi Torizo; Hamada Yoshiki; Takeuchi Isao; Uchiyama Hideko (Fac. Pharm., Meijo Univ., Nagoya, Japan). Yakugaku Zasshi 1969, 89(9), 1260–5 (Japan). Various reaction conditions were examd. for the formulation of I, II, III, and IV by the application of hydrogen peroxide to 1,6-naphthyridine in HOAc soln.

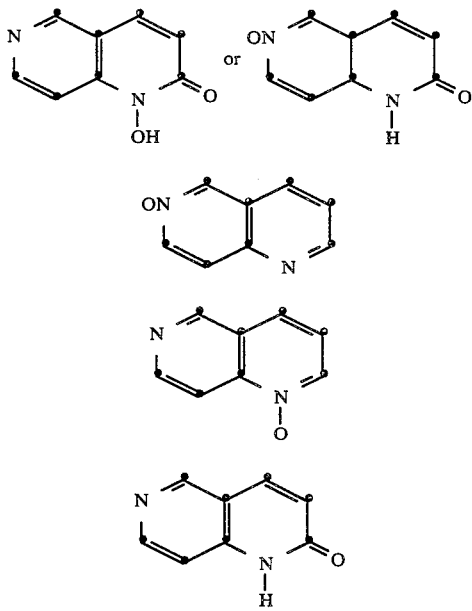

Ir, uv, NMR, and mass spectra of these four compds. were measured to detect their structure, which was detd. by chem. methods such as redn. with Raney Ni. Antibacterial action of I, II, and III was examd."

2-Hydroxy-3-methyl-1,6-naphthyridine, the tautomeric form of 3-methyl-1,6-naphthyridin-2(1H)-one, was reportedly prepared by Ogata et al. [Chem. Pharm. Bull. 20, 2264 (1972)] in two steps by first photocylization of N-(4-pyridinyl)methacrylamide to produce 1,2,3,4-tetrahydro-3-methyl-2-oxo-1,6-naphthyridine and then dehydrogenating said tetrahydro compound by heating it in acetic acid.

SUMMARY OF THE INVENTION

In a composition of matter aspect, the invention resides in 4-R'-5-Q-1,6-naphthyridin-2(1H)-one having the formula I

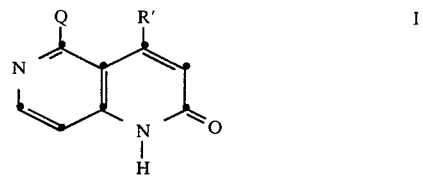

or acid-addition salt thereof, where R' is hydrogen or methyl, and Q is hydroxymethyl, 1-hydroxyethyl, alkanoyloxymethyl or 1-alkanoyloxyethyl. The compounds of formula I where Q is hydroxymethyl, 1-hydroxyethyl or alkanoyloxymethyl are useful as cardiotonic agents, as determined by standard pharmacological evaluation procedures; and, the compounds of formula I where Q is 1-alkanoyloxyethyl are useful as intermediates for preparing the compounds of formula I where Q is 1-hydroxyethyl.

A composition aspect of the invention resides in the cardiotonic composition for increasing cardiac contractility, said composition comprising a pharmaceutically acceptable inert carrier and, as the active component thereof, a cardiotonically effective amount of 4-R'-5-Q-1,6-naphthyridin-2(1H)-one having formula I, where R' is hydrogen or methyl and Q is hydroxymethyl, 1-hydroxyethyl or alkanoyloxymethyl, or pharmaceutically acceptable acid-addition salt thereof.

In a method aspect, the invention resides in the method for increasing cardiac contractility in a patient requiring such treatment which comprises administering orally or parenterally in a solid or liquid dosage form to such patient a cardiotonically effective amount of 4-R'-5-Q-1,6-naphthyridin-2(1H)-one having formula I, where R' is hydrogen or methyl and Q is hydroxymethyl, 1-hydroxyethyl or alkanoyloxymethyl, or pharmaceutically acceptable acid-addition salt thereof.

In another composition of matter aspect, the invention resides in 4-R'-5-Q'-1,6-naphthyridin-2(1H)-one-6-oxide having the formula II

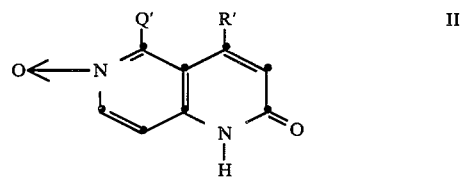

or acid-addition salt thereof, where R' is hydrogen or methyl and Q' is methyl or ethyl. The compounds of formula II are intermediates for preparing compounds of formula I and also are useful as cardiotonic agents, as determined by standard pharmacological evaluation procedures.

A composition of the invention resides in the cardiotonic composition for increasing cardiac contractility, said composition comprising a pharmaceutically acceptable inert carrier and, as the active component thereof, a cardiotonically effective amount of 4-R'-5-Q'-1,6-naphthyridin-2(1H)-one-6-oxide having formula II, where R' and Q' are defined as in formula II, or pharmaceutically acceptable acid-addition salt thereof.

In a method aspect, the invention resides in the method for increasing cardiac contractility in a patient requiring such treatment which comprises administering orally or parenterally in a solid or liquid dosage form to such patient a cardiotonically effective amount of 4-R'-5-Q'-1,6-naphthyridin-2(1H)-one-6-oxide having formula II, where R' and Q' are defined as in formula II, or pharmaceutically acceptable acid-addition salt thereof.

In a process aspect, the invention resides in the process which comprises reacting 4-R'-5-acetyl(or n-propanoyl)-6-[2-(di-lower-alkylamino)ethenyl]-2(1H)-pyridinone having formula III

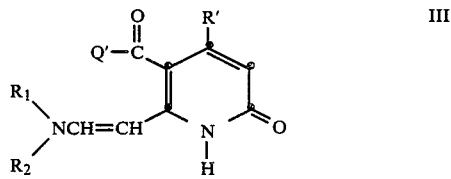

where Q' is methyl or ethyl, R' is hydrogen or methyl, and $R_1$ and $R_2$ are each lower-alkyl, with hydroxylamine or salt thereof to produce 4-R'-5-Q'-1,6-naphthyridin-2(1H)-one-6-oxide having formula II.

In another process aspect, the invention resides in the process which comprises reacting 4-R'-5-Q'-1,6-naphthyridin-2(1H)-one-6-oxide of formula II with an alkanoic anhydride to produce, when Q' is methyl, the compound of formula I where Q is alkanoyloxymethyl or, when Q' is ethyl the compound of formula I where Q is 1-alkanoyloxyethyl, and hydrolyzing said compound of formula I where Q is alkanoyloxymethyl or 1-alkanoyloxyethyl to produce respectively the compound of formula I where Q is hydroxymethyl or 1-hydroxyethyl.

DETAILED DESCRIPTION INCLUSIVE OF PREFERRED EMBODIMENTS

Preferred embodiments having formula I are those where R' is hydrogen and Q is hydroxymethyl or alkanoyloxymethyl, alkanoyl having from one to six carbon atoms.

Preferred embodiments having formula II are those where R' is hydrogen.

The term "alkanoyl" as used herein, e.g., in the definition Q as alkanoyloxymethyl or 1-alkanoylethyl, means alkanoyl radicals having from one to eight carbon atoms which can be arranged as straight or branched chains, illustrated by formyl, acetyl, propionyl (n-propanoyl), butyryl (n-butanoyl), isobutyryl (2-methyl-n-propanoyl), caproyl (n-hexanoyl), caprylyl (n-octanoyl), and the like.

The term "lower-alkyl" as used herein, e.g., as the meaning for $R_1$ or $R_2$ in formula III, means alkyl radicals having from one to four carbon atoms which can be arranged as straight or branched chains, illustrated by methyl, ethyl, n-propyl, isopropyl, n-butyl, 2-butyl and isobutyl.

The compounds of the invention having formulas I and II are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base of the cardiotonically active compounds of the invention are not vitiated by side effects ascribable to the anions. In practicing the invention, it is convenient to use the free base form or the hydrochloric acid-addition salt; however, other appropriate pharmaceutically acceptable salts within the scope of the invention are those derived from mineral acids such as sulfuric acid, phosphoric acid and sulfamic acid; and organic acids such as acetic acid, citric acid, lactic acid, tartaric acid, methanesulfonic acid, ethanesulfonic acid, benzensulfonic acid, p-toluenesulfonic acid, cyclohexylsulfamic acid, quinic acid, and the like, which give the sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, by the correspondence of calculated and found values for the elementary analyses, and, by their method of preparation.

The manner of making and using the instant invention will now be generally described so as to enable a person skilled in the art of pharmaceutical chemistry to make and use the same, as follows.

The reaction of 4-R'-5-acetyl(or n-propanoyl)-6-[2-(di-lower-alkylamino)ethenyl]-2(1H)-pyridinone (III) with hydroxylamine or salt thereof to produce 4-R'-5-Q'-1,6-naphthyridin-2(1H)-one-6-oxide (II) is run by mixing the reactants at room temperature or warming the mixture up to about 100° C. if necessary to effect dissolution and reaction. The reaction is conveniently run using hydroxylamine hydrochloride in water or in aqueous medium containing other water-miscible solvents, e.g., acetic acid, methanol, or in aqueous hydrochloric acid, e.g., 6N HCl, and preferably isolating II as its hydrochloride salt.

The conversion of 4-R'-5-Q'-1,6-naphthyridin-2(1H)-one-6-oxide (II) to 4-R'-5-Q-1,6-naphthyridin-2(1H)-one (I) is carried out by heating II with an alkanoic anhydride, preferably using excess anhydride as solvent if necessary. The reaction temperature can range from about 70° C. to 150° C., preferably about 90° C. to 150° C. Said reaction produces the esters of formula I where Q is alkanoyloxymethyl or 1-alkanoyloxyethyl. The corresponding alcohols (I where Q is hydroxymethyl or 1-hydroxyethyl) are prepared by hydrolyzing said esters, preferably by heating with aqueous alkali.

The above intermediate 4-R'-5-acetyl(or n-propanoyl)-6-[2-(di-lower-alkylamino)ethenyl]-2(1H)-pyridinones (III), which are disclosed and claimed in copending application Ser. No. 404,454, filed Aug. 2, 1982, were prepared by reacting 4-R'-5-acetyl(or n-propanoyl)-6-methyl-2(1H)-pyridinone with di-(lower-alkyl)formamide di-(lower-alkyl) acetal by mixing the reactants at about 35° to 100° C.

The preparation of the intermediate 4-R'-5-acetyl(or n-propanoyl)-6-methyl-2(1H)-pyridinones, which are disclosed and claimed in said copending application Ser. No. 357,872, filed Mar. 15, 1982 and now U.S. Pat. No. 4,412,077, issued Oct. 25, 1983, are described in the following two paragraphs.

The preparation of 5-acetyl(or n-propanoyl)-6-methyl-2(1H)-pyridinone or 5-acetyl(or n-propanoyl)-4,6-dimethyl-2(1H)-pyridinone is carried out by heating at about 100° C. to 150° C. 2-(RCO)-1-methyl-ethenamine (R is lower-alkyl) with a lower-alkyl, preferably methyl or ethyl, 2-propynoate or 2-butynoate, respectively, with or without a suitable solvent.

The intermediate 2-(RCO)-1-methyl-ethenamines are generally known compounds which are prepared by conventional means, as illustrated hereinbelow in the specific exemplary disclosure.

The following examples will further illustrate the invention without, however, limiting it thereto.

A. 4-R'-5-ACETYL(OR n-PROPANOYL)-6-METHYL-2(1H)-PYRIDINONES

A-1. 5-Acetyl-6-methyl-2(1H)-pyridinone—A mixture containing 100 g of 2,4-pentanedione, 200 ml of ethanol and 60 ml of a concentrated aqueous ammonium hydroxide was allowed to stand at room temperature over the weekend (3 days) and then concentrated on a rotary evaporator to yield 83 g of 4-amino-3-penten-2-one as an oil. To the stirred oil was added 70 ml of methyl 2-propynoate over a 10 minute period and the resulting solution was stirred at ambient temperature for 30 minutes whereupon a vigorous exothermic reaction took place. After the exothermic reaction had subsided, the reaction mixture was heated on a steam bath for 2.5 hours, the reaction mixture was then dissolved in 300 ml of boiling isopropyl alcohol, the solution treated with decolorizing charcoal and filtered, and the filtrate concentrated on a rotary evaporator to yield a viscous liquid. To the viscous liquid was added 300 ml of ether and the mixture triturated and allowed to stand at room temperature overnight. The separated solid was collected, washed with ether and dried to yield 84.6 g of material whose nmr spectrum indicated it to be the uncyclized intermediate, methyl 4-acetyl-5-amino-2,4-hexadienoate. [In another run this compound was isolated, recrystallized from methanol and found to melt at 104°-106° C.] The mother liquor from the above was concentrated on a rotary evaporator to a constant weight of 45.6 g of dark oil. The oil was combined with the uncyclized material and dissolved in 250 ml of dimethylformamide and the resulting mixture was refluxed for 4.5 hours. The reaction mixture was allowed to stand at room temperature overnight whereupon a crystalline product separated. The crystalline precipitate was collected, washed with isopropyl alcohol, dried in a vacuum oven at 90°-95° C. to yield 62.5 g of 5-acetyl-6-methyl-2(1H)-pyridinone, m.p. 196°-198° C. The mother liquor from the above was concentrated to dryness on a rotary evaporator and the residue dissolved in 100 ml of isopropyl alcohol, the alcohol solution treated with decolorizing charcoal and filtered and the filtrate allowed to stand at room temperature overnight. The precipitate that separated was collected to yield another 15.2 g of 5-acetyl-6-methyl-2(1H)-pyridinone, m.p. 194°-196° C.

A-2. 6-Methyl-5-(n-propanoyl)-2(1H)-pyridinone—A mixture containing 25 g of 2,4-hexanedione, 100 ml of ethanol and 25 ml of concentrated aqueous ammonium hydroxide was allowed to stand at room temperature overnight and then concentrated on a rotary evaporator to give 21 g, as a pale yellow oil, a mixture containing 4-amino-3-hexen-2-one and 5-amino-4-hexen-3-one. To the oil was added 18.5 g of methyl 2-propynoate and the mixture heated in a oil bath at about 100° C. whereupon a vigorous exothermic reaction took place. After the reaction had subsided, the reaction mixture was heated in an oil bath at 160°-170° C. for 2 hours and then concentrated on a rotary evaporator to give a gummy material. The latter was crystallized from isopropyl alcohol-ether to yield 64 g of 6-methyl-5-(n-propanoyl)-2(1H)-pyridinone, m.p. 173°-175° C., whose structure was confirmed by its NMR spectrum.

A-3. 5-Acetyl-4,6-dimethyl-2(1H)-pyridinone—A mixture containing 40 g of 2,4-pentanedione, 100 ml of ethanol and 50 ml of concentrated aqueous ammonium hydroxide was allowed to stand at room temperature for 6 hours and then concentrated on a rotary evaporator to yield, as an oil, 35.4 g of 4-amino-3-penten-2-one. The oil was dissolved in 100 ml of dimethylformamide and to the solution was added 32 g of methyl 2-butynoate and the resulting reaction mixture was refluxed for 95 hours and then concentrated on a rotary evaporator. The remaining oil residue was heated with 100 ml of ether whereupon a white solid crystallized spontaneously. The solid weas collected, washed with ether and dried in a vacuum oven at 90°-95° C. to yield 25.7 g of 5-acetyl-4,6-dimethyl-2(1H)-pyridinone, m.p. 160°-162° C.

B. 4-R'-5-ACETYL(OR n-PROPANOYL)-6-[2-(DI-LOWER-ALKYLAMINO)ETHENYL]-2(1H)-PYRIDINONES

B-1. 5-Acetyl-6-(2-dimethylaminoethenyl)-2(1H)-pyridinone—A mixture containing 15.1 g of 5-acetyl-6-methyl-2(1H)-pyridinone, 200 ml of dimethylformamide and 15 ml of dimethylformamide dimethyl acetal was stirred at room temperature for 30 minutes, heated gently with stirring on a steam bath for 2 hours, then allowed to cool and stirred at room temperature overnight. The golden yellow needles that separated were collected, washed with methanol and dried in a vacuum oven at 80° C. to yield 10.7 g of 5-acetyl-6-(2-dimethylaminoethenyl)-2(1H)-pyridinone, m.p. 238°–240° C.

B-2. 6-(2-Dimethylaminoethenyl)-5-(n-propanoyl)-2(1H)-pyridinone—A mixture containing 25 g of 6-methyl-5-(n-propanoyl)-2(1H)-pyridinone, 200 ml of dimethylformamide and 25 ml of dimethylformamide dimethyl acetal was heated on a steam bath for 5 and ½ hours and the dimethylformamide was removed by heating the reaction mixture on a rotary evaporator. The residue was refluxed with 100 ml of ethanol, the mixture cooled, and the yellow solid was collected, washed with ethanol and dried in an oven at 90°–95° C. to yield 12.8 g of 6-(2-dimethylaminoethenyl)-5-(n-propanoyl)-2(1H)-pyridinone, m.p. 204°–206° C.

B-3. 5-Acetyl-6-(2-dimethylaminoethenyl)-4-methyl-2(1H)-pyridinone—Following the procedure described in Example B-1 but using in place of 5-acetyl-6-methyl-2(1H)-pyridinone a molar equivalent quantity of 5-acetyl- 4,6-dimethyl-2(1H)-pyridinone, it is contemplated that 5-acetyl-6-(2-dimethylaminoethenyl)-4-methyl-2(1H)-pyridinone can be obtained.

C.
4-R'-5-Q'-1,6-NAPTHYRIDIN-2(1H)-ONE-6-OXIDES

C-1. 5-Ethyl-1,6-naphthyridin-2(1H)-one-6-oxide—A mixture containing 35 g of 5-n-propanoyl-6-(2-dimethylaminoethenyl)-2(1H)-pyridinone, 21 g of hydroxylamine hydrochloride and 200 ml of water was stirred at room temperature for 5 hours and allowed to stand at room temperature overnight (about 15 hours). The yellow crystalline product was collected and dried in vacuo at 95° C. The mother liquor was concentrated to dryness and the solid residue was treated with 50 ml of water. Additional crystalline product was collected, washed with ethanol and dried in vacuo at 95° C. The combined crystalline product, 5-ethyl-1,6-naphthyridin-2(1H)-one-6-oxide as its hemihydrate melted at 262°–264° C. with decomposition. The mother liquor yielded another 2.4 g of product, m.p. 260°–262° C.

Acid-addition salts of 5-ethyl-1,6-naphthyridin-2(1H)-one-6-oxide are conveniently prepared by adding to a mixture of 1 g of 5-ethyl-1,6-naphthyridin-2(1H)-one-6-oxide in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring a molar equivalent quantities each of 5-ethyl-1,6-naphthyridin-2(1H)-one-6-oxide and the appropriate acid, e.g., lactic acid or hydrochloric acid, to prepare respectively the lactate or hydrochloride salt of 5-ethyl-1,6-naphthyridin-2(1H)-one-6-oxide in aqueous solution.

Also, 5-ethyl-1,6-naphthyridin-2(1H)-one-6-oxide as its hydrochloride salt is conveniently prepared following the procedure described in the second paragraph of Example C-2 using a molar equivalent quantity of 6-(2-dimethylaminoethenyl)-5-(n-propanoyl)-2(1H)-pyridinone in place of 5-acetyl-6-(2-dimethylaminoethenyl)-2(1H)-pyridinone.

C-2. 5-Methyl-1,6-naphthyridin-2(1H)-one-6-oxide, m.p. 272°–273° C. with decomposition, can be produced following the procedure described in Example C-1 using a molar equivalent quantity of 5-acetyl-6-(2-dimethylaminoethenyl)-2(1H)-pyridinone in place of 6-(2-dimethylaminoethenyl)-5-(n-propanoyl)-2(1H)-pyridinone.

5-Methyl-1,6-naphthyridin-2(1H)-one-6-oxide as its hydrochloride was prepared as follows: A mixture containing 68 g of 5-acetyl-6-(2-dimethylaminoethenyl)-2(1H)-pyridinone, 68 g of hydroxylamine hydrochloride in 150 ml of 6N aqueous hydrochloric acid was warmed on a steam bath until dissolution resulted. The reaction solution was heated for about 20 minutes and then allowed to stand at room temperature overnight. The separated product was collected, dried and found to melt at 244°–245° C. Additional product was obtained by concentrating the mother liquor to dryness, dissolving the residue in boiling methanol, allowing the solution to cool, collecting the precipitate and drying it in a vacuum oven. The combined product, 5-methyl-1,6-naphthyridin-2(1H)-one-6-oxide hydrochloride, m.p. 244°–245° C., weighed 56 g.

Other acid-addition salts of 5-methyl-1,6-naphthyridin-2(1H)-one-6-oxide are conveniently prepared by adding to a mixture of 1 g of 5-methyl-1,6-naphthyridin-2(1H)-one-6-oxide in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 5-methyl-1,6-naphthyridin-2(1H)-one-6-oxide and the appropriate acid, e.g., lactic acid or hydrochloric acid, to prepare respectively the lactate or hydrochloride salt of 5-methyl-1,6-naphthyridin-2(1H)-one-6-oxide in aqueous solution.

C-3. 4,5-Dimethyl-1,6-naphthyridin-2(1H)-one-6-oxide—Following the procedure described in Example C-1 but using in place of 5-n-propanoyl-6-(2-dimethylaminoethenyl)- 2(1H)-pyridinone a molar equivalent quantity of 5-acetyl-6-(2-dimethylaminoethenyl)-4-methyl-2(1H)-pyridinone, it is contemplated that 4,5-dimethyl-1,6-naphthyridin-2(1H)-one-6-oxide can be obtained.

D. 4-R'-5-Q-1,6-NAPHTHYRIDIN-2(1H)-ONES

D-1. 5-(1-Hydroxyethyl)-1,6-naphthyridin-2(1H)-one—A solution containing 23 g of 5-ethyl-1,6-naphthyridin-2(1H)-one-6-oxide hemihydrate and 150 ml of concentrated hydrochloric acid was evaporated on a rotary evaporator to produce a solid residue which was dried in an oven at 80°–85° C. The residue was treated with 400 ml of acetic anhydride and the mixure was heated on a steam bath with stirring for 24 hours. The reaction mixture was cooled to room temperature and the solid that separated was collected, washed with chloroform and dried at 95° C. to yield 5.7 g of a mixture consisting primarily of 5-(1-hydroxyethyl)-1,6-naphthyridin-2(1H)-one and its acetate, namely, 5-[1-(acetyloxy)ethyl]-1,6-naphthyridin-2(1H)-one. The mother liquor was concentrated on a rotary evaporator to dryness to yield 15.4 g of said mixture of products. The two mixtures of solid products were combined and treated with 25 ml of 35% aqeous sodium hydroxide solution and 100 ml of water. The resulting aqueous mixture was heated on a steam bath with stirring for 4 hours, acidified with acetic acid and concentrated on a rotary evaporator to dryness. The residue was dissolved in 50 ml of methanol and chromatographed using 200 g of silica gel in a 500 ml sintered glass funnel using ether containing up to 20% of methanol. The eluants containing 20% methanol in ether were combined and evaporated to dryness. The resulting solid residue was recrystallized from isopropyl alcohol and dried in an oven at 90°–95° C. to yield 3.8 g of product 5-(1-hydroxyethyl)-1,6-naphthyridin-2(1H)-one, m.p. 210°–212° C. The mother liquor yielded another 6.8 g of crude product.

Acid-addition salts of 5-(1-hydroxyethyl)-1,6-naphthyridin-2(1H)-one are conveniently prepared by adding to a mixture of 1 g of 5-(1-hydroxyethyl)-1,6-naphthyridin-2(1H)-one in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 5-(1-hydroxyethyl)-1,6-naphthyridin-2(1H)-one and the appropriate acid, e.g., lactic acid or hydrochloric acid, to prepare respectively the lactate or hydrochloride salt of 5-(1-hydroxyethyl)-1,6-naphthyridin-2(1H)-one in aqueous solution.

D-2. 5-Hydroxymethyl-1,6-naphthyridin-2(1H)-one—A mixture containing 5.0 g of 5-methyl-1,6-naphthyridin-2(1H)-one-6-oxide and 50 ml of acetic anhydride was stirred at room temperature for about 15 hours and then heated on a steam bath for about 1 hour. The reaction mixture was heated in vacuo and the remaining solid residue was taken up in 50 ml of water and about 5 ml of 6N aqueous hydrochloric acid. The resulting solution was heated on a steam bath for about 30 minutes and then allowed to stand overnight at room temperature. After tlc analysis indicated that the reaction was not yet completed, the reaction mixture was heated with stirring for another 90 minutes. To the reaction mixture was added 5 ml of concentrated hydrochloric acid and the mixture was heated with stirring for three more hours. To the resulting reaction mixture was added solid potassium carbonate to make the mixture basic and the basic mixture (some solid had precipitated) was allowed to stand at room temperature. The separated solid was collected, recrystallized from water and dried at 60° C. over phosphorous pentoxide to yield 1.5 g of product, m.p. 292°–295° C. with decomposition. Said 1.5 g of product was combined with another 9 g of product obtained in other corresponding runs and the combined material was heated with about 50 ml of water plus 20 ml of 6N hydrochloric acid. The hot mixture (small amount of solid undissolved) was filtered, the undissolved solid washed with about 10 ml of 6N hydrochloric acid and the combined filtrate and washings allowed to cool to room temperature and then chilled in an ice bath. The separated product was collected and dried in a vacuum oven to produce 5 g of 5-hydroxymethyl-1,6-naphthyridin-2(1H)-one as its monohydrochloride, m.p. 294°–300° C. with decomposition.

Acid-addition salts of 5-hydroxymethyl-1,6-naphthyridin-2(1H)-one are conveniently prepared by adding to a mixture of 1 g of 5-hydroxymethyl-1,6-naphthyridin-2(1H)-one in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring a molar equivalent quantities each of 5-hydroxymethyl-1,6-naphthyridin-2(1H)-one and the appropriate acid, e.g., lactic acid or hydrochloric acid, to prepare respectively the lactate or hydrochloride salt of 5-hydroxymethyl-1,6-naphthyridin-2(1H)-one in aqueous solution.

D-3. 5-[(Acetyloxy)methyl]-1,6-naphthyridin-2(1H)-one—A mixture containing 38.2 g of 5-methyl-1,6-naphthyridin-2(1H)-one-6-oxide hydrochloride and 300 ml of acetic anhydride was refluxed with stirring on a steam bath for 48 hours and then the reaction mixture was cooled to room temperature. The separated product was collected, recrystallized from dimethylformamide and dried in vacuo at 80° C. to produce 10.5 g of 5-[(acetyloxy)methyl]-1,6-naphthyridin-2(1H)-one as its hydrochloride, m.p. 162°–165° C. with decomposition.

5-[(Acetyloxy)methyl]-1,6-naphthyridin-2(1H)-one also is conveniently prepared by following the procedure described in Example D-4 below but using a molar equivalent quantity of acetic anhydride in place of n-hexanoic acid anhydride.

D-4. 5-[(n-Hexanoyloxy)methyl]-1,6-naphthyridin-2(1H)-one, alternatively named (1,2-dihydro-2-oxo-1,6-naphthyridin-5-yl)methyl n-hexanoate—A mixture containing 4.88 g of 4-dimethylaminopyridine, 4.28 g of 5-hydroxymethyl-1,6-naphthyridin-2(1H)-one monohydrochloride, 20 ml of triethylamine, 4.5 g of n-hexanoic acid anhydride and 20 ml of acetonitrile was refluxed for about 15 hours, allowed to cool and then chilled. The separated solid was collected and the filtrate was evaporated to dryness. The collected precipitate and the residue obtained by evaporating the filtrate to dryness were combined and taken up in about 250 ml of ether. The ether solution was washed successively with water and 10% aqueous potassium bicarbonate solution. The ether was distilled off in vacuo; and, the residue was recrystallized from methanol and dried to produce 2.8 g of 5-[(n-hexanoyloxy)methyl]-1,6-naphthyridin-2(1H)-one, m.p. 158°–159° C.

D-5. 5-Hydroxymethyl-4-methyl-1,6-naphthyridin-2(1H)-one—Following the procedure described in Example D-1 but using in place of 5-ethyl-1,6-naphthyridin-2(1H)-one-6-oxide a molar equivalent quantity of 4,5-dimethyl-1,6-naphthyridin-2(1H)-one-6-oxide, it is contemplated that 5-hydroxymethyl-4-methyl-1,6-naphthyridin-2(1H)-one can be obtained.

Following the procedure described in Example D-4 but using in place of n-hexanoic acid anhydride a molar equivalent quantity or excess of the appropriate alkanoic acid anhydride, it is contemplated that the compounds of Examples D-6 through D-10 can be obtained.

D-6. 5-[(n-Propanoyloxy)methyl]1,6-naphthyridin-2(1H)-one, using n-propanoic acid anhydride.

D-7. 5-(Formyloxymethyl)-1,6-naphthyridin-2(1H)-one, using a mixture of acetic anhydride and an excess of formic acid (mixture reacts to form a mixed anhydride of formic acid and acetic acid which acts as a formylating agent).

D-8. 5-[(2-Methyl-n-propanoyloxy)methyl]-1,6-naphthyridin-2(1H)-one, using 2-methyl-n-propanoic acid anhydride.

D-9. 5-[(n-Butanoyloxy)methyl]-1,6-naphthyridin-2(1H)-one, using n-butanoic acid anhydride.

D-10. 5-[(n-Octanoyloxy)methyl]-1,6-naphthyridin-2(1H)-one, using n-octanoic acid anhydride.

The following compound, 5-[1-(acetyloxy)ethyl]-1,6-naphthyridin-2(1H)-one, which is outside the scope of the instant invention, was prepared for comparative purposes as follows: A mixture containing 6.8 g of 5-(1-hydroxyethyl)-1,6-naphthyridin-2(1H)-one and 50 ml of acetic anhydride was heated on a steam bath for 5 hours and then allowed to stand at room temperature overnight. The reaction mixture was concentrated on a rotary evaporator and the residue was chromatographed using 200 g of silica gel in a 500 ml sintered glass funnel and 5% methanol in ether to obtain a product which was recrystallized from isopropyl alcohol and dried in an oven at 80°-85° C. to produce 4.1 g of 5-[1-(acetyloxy)ethyl]-1,6-naphthyridin-2(1H)-one, m.p. 185°-187° C.

The usefulness of the cardiotonically active compounds of formulas I and II or pharmaceutically acceptable acid-addition salts thereof as cardiotonic agents is demonstated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated guinea pig atria and papillary muscle procedure, the cardiotonically active compounds of formulas I and II or pharmaceutically acceptable acid-addition salts thereof at doses of 1, 3, 10, 30 and/or 100 µg/ml, were found to cause significant increases, that is, greater than 30%, in papillary muscle force and significant increases, that is, greater than 30%, in right atrial force, while causing a lower percentage increase in right atrial rate. For example, when tested at one or more said dose levels by this procedure in said guinea pig test, the compounds of the invention were found to cause respective increases in papillary muscle force (PMF) and right atrial force (RAF) given in Table A.

TABLE A

| | | In Vitro Cardiotonic Activity | | | |
|---|---|---|---|---|---|
| | Dose | Percentage Increase | | | |
| Example | µg/ml | RAR[a] | RAF[b] | PMF[c] | N[d] |
| C-1 | 10 | 20 | 65 | 47 | 3/5 |
| | 30 | 20 | 48 | 33 | 3/5 |
| C-2 | 100 | 11 | 22 | 45 | 3/5 |
| D-1 | 10 | 38 | 56 | 56 | 3/5 |
| | 30 | 63 | 195 | 96 | 3/5 |
| | 100 | 78 | 321 | 120 | 3/5 |
| D-2 | 3 | 13 | 27 | 34 | 6/10 |
| | 10 | 22 | 41 | 73 | 6/10 |
| D-3 | 1 | 15 | 38 | 58 | 3/5 |
| | 10 | 26 | 110 | 143 | 3/5 |
| | 30 | 41 | 269 | 196 | 3/5 |
| D-4 | 10 | 22 | 67 | 93 | 3/2 |
| | 30 | 30 | 134 | 131 | 3/3 |
| | 100 | 35 | 245 | 186 | 3/3 |

[a]Right atrial rate.
[b]Right atrial force.
[c]Papillary muscle force.
[d]Number of preparations.

5-[1-(Acetyloxy)ethyl]1,6-naphthyridin-2(1H)-one, which is outside the scope of the instant invention, was found to be inactive when tested at 10, 30 and 100 µg/ml in said guinea pig test.

When tested by said anesthetized dog procedure, the cardiotonically active compounds of formulas I and II at doses of 0.10, 0.30, 1.0 and/or 3.0 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples C-1, C-2, D-2, D-3 and D-4 were found to cause increases of about 27% to 226% in contractile force and lower changes in heart rate and blood pressure, the contractile force increases at 0.30 mg/kg i.v. for the compounds of Examples C-1, C-2, D-2, D-3 and D-4 being 77%, 53%, 50%, 109% and 42%, respectively.

The present invention includes within its scope a cardiotonic composition comprising a pharmaceutically acceptable carrier and, as the active component thereof, the cardiotonically active compound of formula I or II or pharmaceutically acceptable acid-addition salt thereof. The invention also includes within its scope the method for increasing cardiac contractility in a patient requiring such treatment which comprises administering to such patient a cardiotonically effective amount of the active compound of formula I or II or pharmaceutically acceptable acid-addition salt thereof. In clinical practice said compound or salt thereof will normally be administered orally or parenterally in a wide variety of dosage forms.

Solid compositions for oral administration include compressed tablets, pills powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmecutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A 4-R'-5-Q-1,6-naphthyridin-2(1H)-one having the formula

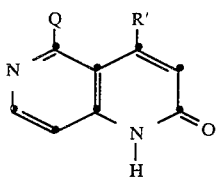

or acid-addition salt thereof, where R' is hydrogen or methyl, and Q is hydroxymethyl, 1-hydroxyethyl, alkanoyloxymethyl or 1-alkanoyloxyethyl, alkanoyl in each instance having from one to eight carbon atoms.

2. A compound according to claim 1 where R' is hydrogen and Q is hydroxymethyl or alkanoyloxymethyl, alkanoyl having from one to six carbon atoms.

3. 5-Hydroxymethyl-1,6-naphthyridin-2(1H)-one according to claim 1.

4. 5-[(Acetyloxy)methyl]-1,6-naphthyridin-2(1H)-one according to claim 1.

5. 5-[(n-Hexanoyloxy)methyl]-1,6-naphthyridin-2(1H)-one according to claim 1.

6. A cardiotonic composition for increasing cardiac contractility, said composition comprising a pharmaceutically acceptable inert carrier and, as the active component thereof, a cardiotonically effective amount of 4-R'-5-Q-1,6-naphthyridin-2(1H)-one according to claim 1 where Q is hydroxymethyl, 1-hydroxyethyl or alkanoyloxymethyl or pharmaceutically acceptable acid-addition salt thereof, alkanoyl having from one to eight carbon atoms.

7. The method for increasing cardiac contractility in a patient requiring such treatment which comprises administering orally or partenterally in a solid or liquid dosage form to such patient a cardiotonically effective amount of 4-R'-5-Q-1,6-naphthyridin-2(1H)-one according to claim 1 where Q is hydroxymethyl, 1-hydroxyethyl or alkanoyloxymethyl or pharmaceutically acceptable acid-addition salt thereof, alkanoyl having from one to eight carbon atoms.

* * * * *